(12) United States Patent
Wahlstrand et al.

(10) Patent No.: US 7,212,864 B2
(45) Date of Patent: May 1, 2007

(54) MODULAR IMPLANTABLE MEDICAL DEVICE

(75) Inventors: Carl D. Wahlstrand, Lino Lakes, MN (US); Ruchika Singhal, Minneapolis, MN (US); Robert M. Skime, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 10/731,638

(22) Filed: Dec. 9, 2003

(65) Prior Publication Data

US 2004/0176817 A1    Sep. 9, 2004

Related U.S. Application Data

(60) Provisional application No. 60/507,857, filed on Oct. 1, 2003, provisional application No. 60/503,946, filed on Sep. 20, 2003, provisional application No. 60/503,945, filed on Sep. 20, 2003, provisional application No. 60/471,262, filed on May 16, 2003, provisional application No. 60/431,854, filed on Dec. 9, 2002.

(51) Int. Cl.
*A61N 1/375* (2006.01)

(52) U.S. Cl. ............................................ 607/36

(58) Field of Classification Search .............. 623/11; 607/116, 36, 2, 57, 45
See application file for complete search history.

(56) References Cited

U.S. PATENT DOCUMENTS

| | | | |
|---|---|---|---|
| 3,522,811 A | 8/1970 | Schwartz et al. | |
| 3,690,325 A | 9/1972 | Kenny | |
| 3,724,467 A | 4/1973 | Avery et al. | |
| 3,913,587 A | 10/1975 | Newash | |
| 4,010,760 A | 3/1977 | Kraska et al. | |
| 4,013,081 A | 3/1977 | Kolenik | |
| 4,040,412 A | 8/1977 | Sato | |
| 4,256,115 A | 3/1981 | Bilitch | |
| 4,266,552 A | 5/1981 | Dutcher et al. | |
| 4,328,813 A | 5/1982 | Ray | |
| 4,399,819 A | 8/1983 | Cowdery | |
| 4,399,820 A | 8/1983 | Wirtzfeld et al. | |
| 4,499,907 A | 2/1985 | Kallok et al. | |
| 4,616,655 A | 10/1986 | Weinberg et al. | |
| 4,911,178 A | 3/1990 | Neal | |

(Continued)

FOREIGN PATENT DOCUMENTS

DE    3940632    12/1990

(Continued)

OTHER PUBLICATIONS

Notification of Transmittal of the International Search Report dated May 14, 2004, International Application No. PCT/US03/38981.

(Continued)

*Primary Examiner*—Scott M. Getzow
(74) *Attorney, Agent, or Firm*—Shumaker & Sieffert, P.A.

(57) ABSTRACT

An implantable medical device for implantation in the head of a patient. The implantable medical device has a plurality of interconnected modules one or more of which are covered by an overmold and one or more of which are partially covered by the overmold. The module(s) covered by the overmold may be implanted between the cranium and scalp, while the module(s) partially covered by the overmold may be placed at least partially into a recess in the cranium.

23 Claims, 16 Drawing Sheets

U.S. PATENT DOCUMENTS

| | | |
|---|---|---|
| 4,928,696 A | 5/1990 | Henderson et al. |
| 4,969,899 A | 11/1990 | Cox, Jr. |
| 4,972,846 A | 11/1990 | Owens et al. |
| 5,085,644 A | 2/1992 | Watson et al. |
| 5,197,332 A | 3/1993 | Shennib |
| 5,271,397 A | 12/1993 | Seligman et al. |
| 5,314,451 A | 5/1994 | Mulier |
| 5,314,453 A | 5/1994 | Jeutter |
| 5,411,537 A | 5/1995 | Munshi et al. |
| H1465 H | 7/1995 | Stokes |
| 5,455,999 A | 10/1995 | Owens et al. |
| 5,477,855 A | 12/1995 | Schindler et al. |
| 5,489,225 A | 2/1996 | Julian |
| 5,554,194 A | 9/1996 | Sanders |
| 5,562,715 A | 10/1996 | Czura et al. |
| 5,571,148 A | 11/1996 | Loeb et al. |
| 5,613,935 A | 3/1997 | Jarvik |
| 5,638,832 A | 6/1997 | Singer et al. |
| 5,645,586 A * | 7/1997 | Meltzer .................. 623/11.11 |
| 5,678,559 A | 10/1997 | Drakulic |
| 5,702,430 A | 12/1997 | Slimon et al. |
| 5,741,313 A | 4/1998 | Nason et al. |
| 5,755,743 A | 5/1998 | Volz et al. |
| 5,769,874 A | 6/1998 | Dahlberg |
| 5,776,169 A | 7/1998 | Schroeppel |
| 5,800,535 A | 9/1998 | Howard, III |
| 5,814,095 A | 9/1998 | Müller et al. |
| 5,843,150 A | 12/1998 | Adams et al. |
| 5,895,414 A | 4/1999 | Sanchez-Zambrano |
| 5,896,647 A | 4/1999 | Shkuratoff |
| 5,919,215 A | 7/1999 | Haeg et al. |
| 5,935,154 A | 8/1999 | Westlund |
| 5,941,905 A | 8/1999 | Single |
| 5,941,906 A | 8/1999 | Barreras, Sr. et al. |
| 5,954,751 A | 9/1999 | Chen et al. |
| 5,954,757 A | 9/1999 | Gray |
| 5,984,859 A | 11/1999 | Lesinski |
| 5,991,664 A | 11/1999 | Seligman |
| 6,006,124 A | 12/1999 | Fischell et al. |
| 6,016,449 A | 1/2000 | Fischell et al. |
| 6,016,593 A | 1/2000 | Kyrstein |
| 6,061,593 A | 5/2000 | Fischell et al. |
| 6,067,474 A | 5/2000 | Schulman et al. |
| 6,091,979 A | 7/2000 | Madsen |
| 6,128,538 A | 10/2000 | Fischell et al. |
| 6,131,581 A | 10/2000 | Leysieffer et al. |
| 6,134,474 A | 10/2000 | Fischell et al. |
| 6,168,580 B1 | 1/2001 | Yardley |
| 6,176,879 B1 | 1/2001 | Reischl et al. |
| 6,214,032 B1 | 4/2001 | Loeb et al. |
| 6,230,049 B1 | 5/2001 | Fischell et al. |
| 6,248,080 B1 | 6/2001 | Miesel et al. |
| 6,259,951 B1 | 7/2001 | Kuzma et al. |
| 6,266,556 B1 | 7/2001 | Ives et al. |
| 6,269,266 B1 | 7/2001 | Leysieffer |
| 6,272,382 B1 | 8/2001 | Faltys et al. |
| 6,308,101 B1 | 10/2001 | Faltys et al. |
| 6,324,428 B1 | 11/2001 | Weinberg et al. |
| 6,330,468 B1 | 12/2001 | Scharf |
| 6,354,299 B1 | 3/2002 | Fischell et al. |
| 6,356,792 B1 | 3/2002 | Zonenshayn et al. |
| 6,358,281 B1 | 3/2002 | Berrang et al. |
| 6,360,122 B1 | 3/2002 | Fischell et al. |
| 6,427,086 B1 | 7/2002 | Fischell et al. |
| 6,445,956 B1 | 9/2002 | Laird et al. |
| 6,480,743 B1 | 11/2002 | Kirkpatrick et al. |
| 6,490,486 B1 | 12/2002 | Bradley |
| 6,516,227 B1 | 2/2003 | Meadows et al. |
| 6,537,200 B2 | 3/2003 | Leysieffer et al. |
| 6,554,762 B2 | 4/2003 | Leysieffer |
| 6,560,486 B1 | 5/2003 | Osorio et al. |
| 6,565,503 B2 | 5/2003 | Leysieffer et al. |
| 6,567,703 B1 | 5/2003 | Thompson et al. |
| 6,575,894 B2 | 6/2003 | Leysieffer et al. |
| 6,597,954 B1 | 7/2003 | Pless et al. |
| 6,618,623 B1 | 9/2003 | Pless et al. |
| 6,626,680 B2 | 9/2003 | Ciurzynski et al. |
| 6,648,914 B2 | 11/2003 | Berrang et al. |
| 6,671,544 B2 | 12/2003 | Baudino |
| 6,726,678 B1 | 4/2004 | Nelson et al. |
| 6,788,974 B2 | 9/2004 | Bardy et al. |
| 6,805,998 B2 | 10/2004 | Jenson et al. |
| 6,977,124 B2 | 12/2005 | Probst et al. |
| 7,103,415 B2 | 9/2006 | Probst et al. |
| 2001/0033953 A1 | 10/2001 | Takeuchi et al. |
| 2001/0051819 A1 | 12/2001 | Fischell et al. |
| 2002/0002390 A1 | 1/2002 | Fischell et al. |
| 2002/0013612 A1 | 1/2002 | Whitehurst |
| 2002/0019669 A1 | 2/2002 | Berrang et al. |
| 2002/0051550 A1 | 5/2002 | Leysieffer |
| 2002/0068958 A1 | 6/2002 | Bardy et al. |
| 2002/0099412 A1 | 7/2002 | Fischell et al. |
| 2002/0103510 A1 | 8/2002 | Bardy et al. |
| 2002/0161403 A1 | 10/2002 | Meadows et al. |
| 2002/0165588 A1 | 11/2002 | Fraley et al. |
| 2002/0169485 A1 | 11/2002 | Pless et al. |
| 2003/0004428 A1 | 1/2003 | Pless et al. |
| 2003/0004546 A1 | 1/2003 | Casey |
| 2003/0040781 A1 | 2/2003 | Sunderland et al. |
| 2003/0073972 A1 | 4/2003 | Rosenman et al. |
| 2003/0085684 A1 | 5/2003 | Tsukamoto et al. |
| 2003/0088294 A1 | 5/2003 | Gesotti |
| 2003/0109903 A1 | 6/2003 | Berrang et al. |
| 2003/0130706 A1 | 7/2003 | Sheffield et al. |
| 2003/0171787 A1 | 9/2003 | Money et al. |
| 2004/0082977 A1 | 4/2004 | Engmark et al. |

FOREIGN PATENT DOCUMENTS

| | | |
|---|---|---|
| GB | 1 161 579 | 8/1969 |
| WO | WO 92/20402 | 11/1992 |
| WO | WO 00/013743 | 3/2000 |
| WO | WO 01/010369 | 2/2001 |
| WO | WO 01/28622 | 4/2001 |
| WO | WO 01/39830 | 6/2001 |
| WO | WO 01/041858 | 6/2001 |
| WO | WO 01/060450 | 8/2001 |
| WO | WO 01/097906 | 12/2001 |
| WO | WO 02/005590 | 1/2002 |
| WO | WO 02/056637 | 7/2002 |
| WO | WO 03/026739 | 4/2003 |
| WO | WO 03/076012 | 9/2003 |
| WO | WO 04/043536 | 5/2004 |
| WO | WO 04/052458 | 6/2004 |

OTHER PUBLICATIONS

Written Opinion dated Dec. 16, 2004, International Application No. PCT/US03/38981.

Notification of Transmittal of the International Preliminary Examination Report dated Apr. 11, 2005, International Application No. PCT/US03/38981.

U.S. Appl. No. 10/837,319, filed Apr. 30, 2004, entitled "Implantable Medical Device With Anti-Infection Agent".

U.S. Appl. No. 10/835,527, filed Apr. 29, 2004, entitled "Implantation of Implantable Medical Device".

U.S. Appl. No. 10/835,232, filed Apr. 29, 2004, entitled "Explanation of Implantable Medical Device".

U.S. Appl. No. 10/835,233, filed Apr. 29, 2004, entitled "Implantable Medical Device With A Nonhermetic Battery".

U.S. Appl. No. 10/835,548, filed Apr. 29, 2004, entitled "Headset Recharger For Cranially Implantable Medical Devices".

U.S. Appl. No. 10/835,245, filed Apr. 29, 2004, entitled "Battery Housing Configuration".

U.S. Appl. No. 10/837,276, filed Apr. 30, 2004, entitled "Implantable Medical Device With Lubricious Material".

U.S. Appl. No. 10/731,868, filed Dec. 9, 2003, entitled "Implantation of Low-Profile Implantable Medical Device".

U.S. Appl. No. 10/731,699, filed Dec. 9, 2003, entitled "Coupling Module of a Modular Implantable Medical Device".

U.S. Appl. No. 10/730,873, filed Dec. 9, 2003, entitled "Overmold for a Modular Implantable Medical Device".

U.S. Appl. No. 10/731,881, filed Dec. 9, 2003, entitled "Reducing Relative Intermodule Motion in a Modular Implantable Medical Device".

U.S. Appl. No. 10/730,878, filed Dec. 9, 2003, entitled "Lead Interconnect Module of a Modular Implantable Medical Device".

U.S. Appl. No. 10/730,877, filed Dec. 9, 2003, entitled "Low-Profile Implantable Medical Device".

U.S. Appl. No. 10/731,867, filed Dec. 9, 2003, entitled "Concavity of an Implantable Medical Device".

U.S. Appl. No. 10/731,869, filed Dec. 9, 2003, entitled "Modular Implantable Medical Device".

"Surgical Process," Animation Screenshots from http://www.cochlearamerica.com/800.asp, 7 pgs (downloaded Feb. 3, 2004).

"Candidates Brochure," http://www.cochlearamerica.com/pdfs/candidatebrochglobal.pdf, 14 pgs (downloaded Feb. 3, 2004).

"Research and Development," http://www.cochlearamericas.com/384.asp, 1 pg (downloaded Feb. 3, 2004).

"The World Leader in cochlear implants—revolutionizing hearing for adults and infants," http://www.cochlear.com, 1 pg (downloaded Feb. 3, 2004).

"Cochlear: innovator of the Nucleus 3 cochlear implant system," http://www.cochlearamericas.com, 1 pg (downloaded Feb. 3, 2004).

"What is a Cochlear Implant," http://cochlearamericas.com/What/161.asp, 1 pg (downloaded Feb. 3, 2004).

"ESPrit 3G Speech Processor," http://www.cochlearamericas.com/591.asp, 2 pgs (downloaded Feb. 3, 2004).

"Nucleus 3 System," http://www.cochlearamericas.com/Products/465.asp, 1 pg (downloaded Feb. 3, 2004).

"Internal Components: Nucleus 24 Cochlear Implants," http://www.cochlearamericas.com/374.asp, 1 pg (downloaded Feb. 3, 2004).

"Nucleus 24 Contour, " http://www.cochlearamericas.com/568.asp, 2 pgs (downloaded Feb. 3, 2004).

"Nucleus 24 K," http://www.cochlearamericas.com/371.asp, 1 pg (downloaded Feb. 3, 2004).

"Nucleus 24 Double Array," http://www.cochlearamericas.com/370.asp, 1 pg (downloaded Feb. 3, 2004).

"Nucleus 24 ABI: Auditory Brainstem Implant," http://www.cochlearamericas.com/373.asp, 2 pgs (downloaded Feb. 3, 2004).

"Nucleus Speech Processors," http://www.cochlearamericas.com/629.asp, 1 pg (downloaded Feb. 3, 2004).

"Sprint: body worn speech processor," http://www.cochlearamericas.com/1010.asp, 1 pg (downloaded Feb. 3, 2004).

"Cochlear," http://www.cochlearamericas.com/Recipients/978.asp, 3 pgs (downloaded Feb. 3, 2004).

* cited by examiner

MODULAR IMPLANTABLE MEDICAL DEVICE

This application claims the benefit of:
1. U.S. Provisional Application entitled "CRANIAL NEUROSTIMULATOR AND METHOD," Ser. No. 60/431,854, filed on Dec. 9, 2002;
2. U.S. Provisional Application entitled "IMPLANTABLE CRANIAL MEDICAL DEVICES AND METHODS," Ser. No. 60/471,262, filed on May 16, 2003;
3. U.S. Provisional Application entitled "IMPLANTABLE CRANIAL MEDICAL DEVICES AND METHODS," Ser. No. 60/503,945, filed on Sep. 20, 2003;
4. U.S. Provisional Application entitled "IMPLANTABLE CRANIAL MEDICAL DEVICES AND METHODS," Ser. No. 60/503,946, filed on Sep. 20, 2003; and
5. U.S. Provisional Application entitled "Thin Neuro Stimulation System, Device and Method," Ser. No. 60/507,857, filed on Oct. 1, 2003.

The entire content of each of these U.S. Provisional Applications is incorporated herein by reference.

The following co-pending and commonly-assigned U.S. patent applications, filed on even date herewith, are also incorporated herein by reference in their entirety:
1. U.S. patent application entitled "CONCAVITY OF AN IMPLANTABLE MEDICAL DEVICE," assigned U.S. Ser. No. 10/731,867;
2. U.S. patent application entitled "REDUCING RELATIVE INTER-MODULE MOTION IN A MODULAR IMPLANTABLE MEDICAL DEVICE," assigned U.S. Ser. No. 10/731,881;
3. U.S. patent application entitled "OVERMOLD FOR A MODULAR IMPLANTABLE MEDICAL DEVICE," assigned U.S. Ser. No. 10/730,873;
4. U.S. patent application entitled "COUPLING MODULE OF A DISTRIBUTED MODULAR IMPLANTABLE MEDICAL DEVICE," assigned U.S. Ser. No. 10/731,699;
5. U.S. patent application entitled "LEAD CONNECTION MODULE OF A MODULAR IMPLANTABLE MEDICAL DEVICE," assigned U.S. Ser. No. 10/730,878;
6. U.S. patent application entitled "LOW-PROFILE IMPLANTABLE MEDICAL DEVICE," assigned U.S. Ser. No. 10/730,877; and
7. U.S. patent application entitled "IMPLANTATION OF LOW-PROFILE IMPLANTABLE MEDICAL DEVICE," assigned U.S. Ser. No. 10/731,868.
8. U.S. patent application entitled "MODULAR IMPLANTABLE MEDICAL DEVICE," to Carl D. Wahlstrand et al., filed Dec. 9, 2003, assigned U.S. Ser. No. 10/731,869.

TECHNICAL FIELD

The invention relates to medical devices, and more particularly, to implantable medical devices that deliver therapy to and/or monitor a patient.

BACKGROUND

Depending on the application for which they are implanted in a patient, implantable medical devices (IMDs) may include a variety of electrical and/or mechanical components. Typically, an IMD includes a rigid housing that houses all of its components, which are generally fragile, to protect the components from forces to which they would otherwise be exposed when implanted within the human body. In order to avoid potentially harmful interactions between the components and bodily fluids, e.g., corrosion, IMD housings are typically hermetically sealed. Many IMD housings are fabricated from Titanium because of its desirable rigidity and biocompatibility.

The size and shape of an IMD housing is dependant on the sizes and shapes of the components of the IMD. Large components common to most IMDs include a battery, a telemetry coil, and a circuit board that carries digital circuits, e.g., integrated circuit chips and/or a microprocessor, and analog circuit components. Attempts have been made to reduce the size of the IMD housing by reducing the size of these components, changing the shape of these components, and organizing these components within the IMD housing to avoid empty space within the housing. Despite these efforts to reduce the size of IMD housings, the size, shape and rigidity of IMD housings still greatly limits the locations within the human body where an IMD can be practically implanted.

Due to these limitations, an IMD is typically implanted within the abdomen, upper pectoral region, or subclavicular region of a patient. Leads or catheters must be used in order to deliver therapy or monitor a physiological parameter at a location of the body other than where the IMD is implanted. Implantation and positioning of leads and catheters can be difficult and time-consuming from the perspective of a surgeon, particularly where the IMD is located a significant distance from the treatment or monitoring site. Moreover, the increased surgical time, increased surgical trauma, and increased amount of implanted material associated with the use of leads and catheters can increase the risk to the patient of complications associated with the implantation of an IMD.

For example, IMDs that are used to treat or monitor the brain, e.g., to deliver deep brain stimulation (DBS) therapy, are implanted some distance away from the brain, e.g., within the subclavicular region of patients. The long leads that connect the implantable medical device to electrodes implanted within the brain require tunneling under the scalp and the skin of the neck, thereby requiring increased surgery and a prolonged amount of time under general anesthesia during the implant procedure, as well as increased recovery time. In some cases, tunneling the leads under the scalp and skin of the neck requires an additional surgical procedure under general anesthesia. The lengthy tract along the leads is more susceptible to infection, and the leads can erode the overlying scalp, forcing removal so that the scalp can heal. Further, the long leads running under the scalp and through the neck are more susceptible to fracture due to torsional and other forces caused by normal head and neck movements.

SUMMARY

The invention is related to an implantable medical device for implantation in the head of a patient. The implantable medical device has a plurality of interconnected modules one or more of which are covered by an overmold and one or more of which are partially covered by the overmold. The module(s) covered by the overmold may be implanted between the cranium and scalp while the module(s) partially covered by the overmold may be placed at least partially into a recess in the cranium. Components of the implantable medical device that may take up more space may be in the partially covered module since that module may be larger. Smaller components may be in the module(s) covered by the overmold.

The details of one or more embodiments of the invention are set forth in the accompanying drawings and the description below. Other embodiments of the invention will be apparent from the description and drawings, and from the claims.

DETAILED DESCRIPTION

Figure 1:
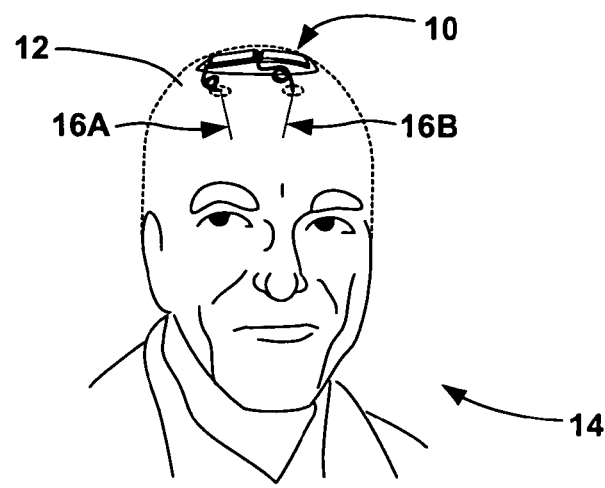
FIG. 1 is a conceptual diagram illustrating an example modular implantable medical device implanted on the cranium of a patient.

FIG. 1 is a conceptual diagram illustrating an example modular implantable medical device (IMD) 10 implanted on the cranium 12 of a patient 14. As will be described in greater detail below, IMD 10 comprises a plurality of separately housed and flexibly interconnected modules. By distributing components of IMD 10 amongst modules rather than including them within a single, rigid housing, the implantable medical device may be shaped and configured for implantation at locations within patient 14 for which implantation of conventional IMDs is deemed undesirable. Further, the flexibility of the interconnection between modules of IMD 10 may allow multiples degrees of freedom of movement between the modules, which in turn may allow the implantable medical device to conform to such areas, and in particular embodiments, to conform to surfaces within patient 14 such as the surface of cranium 12.

In the illustrated example, modular IMD 10 is coupled to two leads 16A and 16B (collectively "leads 16") that extend through holes within cranium 12, and into the brain of patient 14. In exemplary embodiments, each of leads 16 carries a plurality of electrodes, and IMD 10 delivers stimulation to the brain of patient 14 via the electrodes. Modular IMD 10 may be coupled to any number of leads 16, and in some embodiments is not coupled to any leads 16.

Because modular IMD 10 can be implanted on cranium 12 of patient 14 rather then more remotely from the brain of patient 14, such as within an subclavicular region of patient 14, the problems associated with the use of long leads needed to allow a remotely implanted IMDs to access the brain may be diminished or avoided. These problems include the requirement of tunneling under the scalp and the skin of the neck, increased surgery and recovery time, an additional procedure under general anesthesia, risk of infection or skin erosion along the track through which the leads are tunneled, and risk of lead fracture due to torsional and other forces caused by normal head and neck movements.

Figure 2:
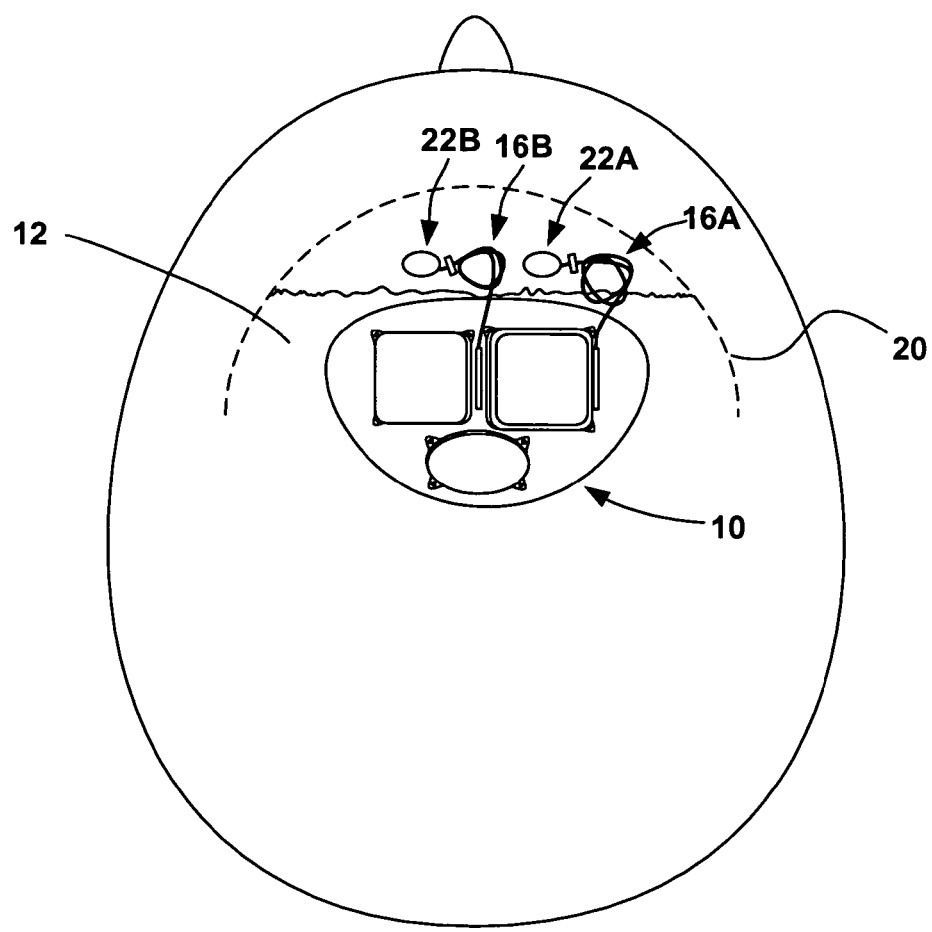
FIG. 2 is a top-view diagram further illustrating the modular implantable medical device of FIG. 1 implanted on the cranium of the patient.

FIG. 2 is a top-view diagram further illustrating modular IMD 10 implanted on cranium 12 of the patient 14. In order to implant modular IMD 10 on cranium 12, an incision 20 is made through the scalp of patient 14, and a resulting flap of skin is pulled back to expose the desired area of cranium 12. The incision may, as shown in FIG. 2, be generally shaped like a "C." Such an incision is commonly referred to as a "C-flap" incision.

Holes 22A and 22B (collectively "holes 22") are drilled through cranium 12, and leads 16 are inserted through holes 22 and into the brain of patient 14. Caps may be placed over holes 22 as is known in the art. Leads 16 are connected to modular IMD 10, either directly or via a lead extension, and modular IMD 10 is placed at least partially within a pocket formed using a hand or a tool beneath the scalp behind holes 22.

Once positioned as desired on cranium 12 within the pocket, modular IMD 10 may then be fixed to cranium 12 using an attachment mechanism such as bone screws. The skin flap may be closed over modular IMD 10, and the incision may be stapled or sutured. The location on cranium 12 at which IMD 10 is illustrated as implanted in FIG. 2 is merely exemplary, and IMD 10 can be implanted anywhere on the surface of cranium 12. Further details regarding exemplary techniques for implanting IMD 10 on the cranium may be found in a commonly-assigned U.S. patent application entitled "IMPLANTATION OF LOW-PROFILE IMPLANTABLE MEDICAL DEVICE," assigned U.S. Ser. No. 10/731,868.

Because of the flexibility provided by interconnect members and/or an overmold of modular IMD 10, the IMD may be manipulated during implantation such that it conforms to cranium 12. For example, in some embodiments a clinician can manipulate modular IMD 10 into conformance with cranium 12 while IMD 10 is on cranium 12 and fix modular IMD 10 into place using bone screws or the like. In other embodiments, the clinician may manipulate modular IMD 10 into conformance with cranium 12 with IMD 10 on and/or off of cranium 12, and IMD 10 may substantially retain the form into which it is manipulated.

As mentioned above, modular IMD 10 may deliver stimulation to the brain of patient 14 to, for example, provide deep brain stimulation (DBS) therapy, or to stimulate the cortex of the brain. Cortical stimulation may involve stimulation of the motor cortex. Modular IMD 10 may be used to treat any nervous system disorder including, but not limited to, epilepsy, pain, psychological disorders including mood and anxiety disorders, movement disorders (MVD), such as, but not limited to, essential tremor, Parkinson's disease, and neurodegenerative disorders.

However, modular IMD 10 is not limited to delivery of stimulation to the brain of patient, and may be employed with leads 16 deployed anywhere in the head or neck including, for example, leads deployed on or near the surface of the skull, leads deployed beneath the skull such as near or on the dura mater, leads placed adjacent cranial or other nerves in the neck or head, or leads placed directly on the surface of the brain. Moreover, modular IMD 10 is not limited to implantation on cranium 12. Indeed, modular IMD 10 may be implanted anywhere within patient 14. For example, modular IMD 10 can be implanted within the neck of patient 14, and deliver stimulation to the vagus nerve or the cervical region of the spinal cord.

Modular IMD 10 may alternatively be implanted within a pectoral region or the abdomen of patient 14 to act as a diaphragmatic pacer, or to provide any of the monitoring and therapy delivery functions known in the art to be associated with cardiac pacemakers. Further, modular IMD 10 may be implanted in the upper buttock region and deliver spinal cord, urological or gastrological stimulation therapy, or may be configured to be implanted within the periphery, e.g., limbs, of patient 14 for delivery of stimulation to the muscles and/or peripheral nervous system of patient 14. As is the case with cranium 12, the modularity of IMD 10 may enable implantation at some of these example locations for which implantation of conventional IMDs is generally deemed undesirable.

Modular IMD 10 is not limited to embodiments that deliver stimulation. For example, in some embodiments modular IMD 10 may additionally or alternatively monitor one or more physiological parameters and/or the activity of patient 14, and may include sensors for these purposes. Where a therapy is delivered, modular IMD 10 may operate in an open loop mode (also referred to as non-responsive operation), or in a closed loop mode (also referred to as responsive). Modular IMD 10 may also provide warnings based on the monitoring.

As discussed above, the ability of a modular IMD 10 according to the invention to be implanted close to a region within patient 14 to be monitored enables the use of shorter leads 16. Shorter leads 16 may advantageously improve the accuracy of such sensors by reducing noise attributable to leads 16. Shorter leads 16 may also advantageously reduce the negative affects of imaging techniques such as magnetic resonance imaging "MRI" on a person implanted with IMD 10.

Further, in some embodiments modular IMD 10 can additionally or alternatively deliver a therapeutic agent to patient 14, such as a pharmaceutical, biological, or genetic agent. Modular IMD 10 may be coupled to a catheter, and may include a pump to deliver the therapeutic agent via the catheter.

Figure 3:
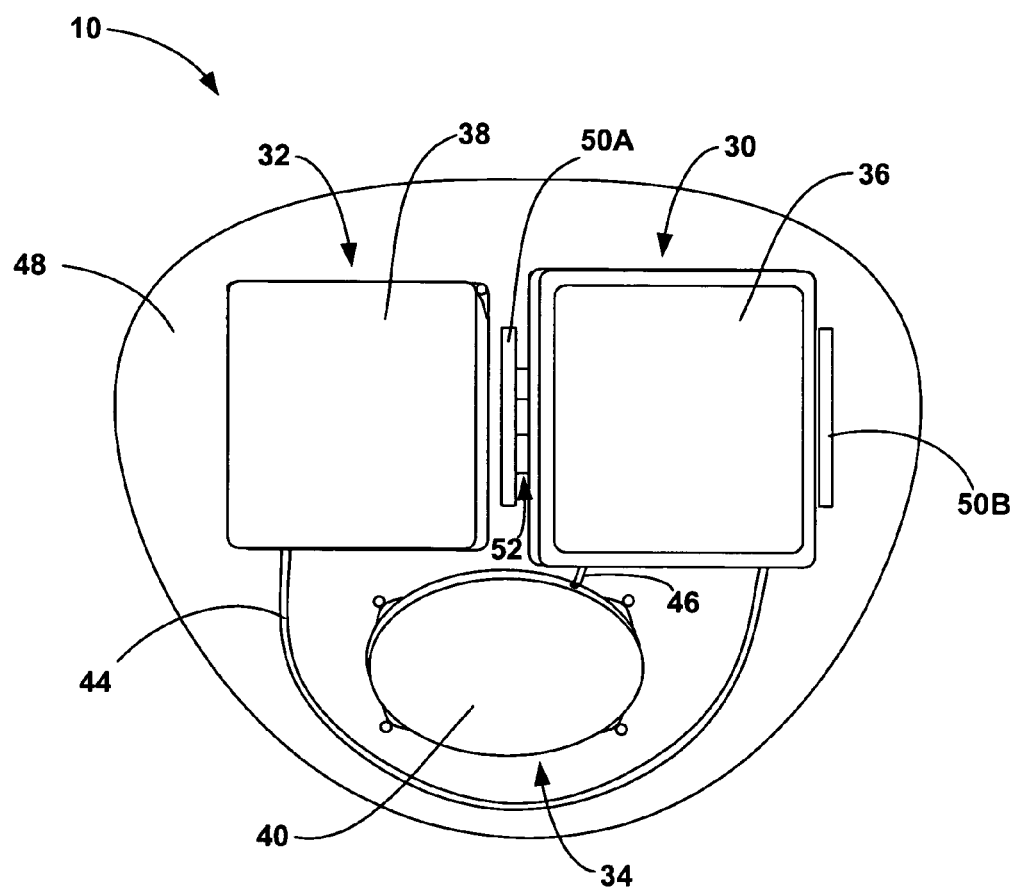
FIG. 3 is a top-view diagram further illustrating the modular implantable medical device of FIG. 1.

FIG. 3 is a top-view diagram further illustrating modular IMD 10. In the illustrated embodiment, modular IMD 10 includes three modules: a control module 30, a power source module 32, and a recharge module 34. As shown in FIG. 3, modules 30, 32 and 34 include separate housings 36, 38 and 40, respectively.

Control module 30 includes control electronics within the housing, e.g., electronics that control the monitoring and/or therapy delivery functions of modular IMD 10, such as a microprocessor. Control module 30 may also include circuits for telemetry communication with external programmers or other devices within the housing. Housing 36 of control module 30 may be hermetic in order to protect the control electronics therein, and in exemplary embodiments is formed of a rigid material, such as titanium, stainless steel, or a ceramic. In exemplary embodiments, housing 36 is a low-profile, concave housing, and techniques for arranging components of control module 30 to enable such a low-profile, concave housing are described in greater detail in a commonly-assigned U.S. patent application entitled "LOW-PROFILE IMPLANTABLE MEDICAL DEVICE," assigned U.S. Ser. No. 10/730,877.

Figure 4:
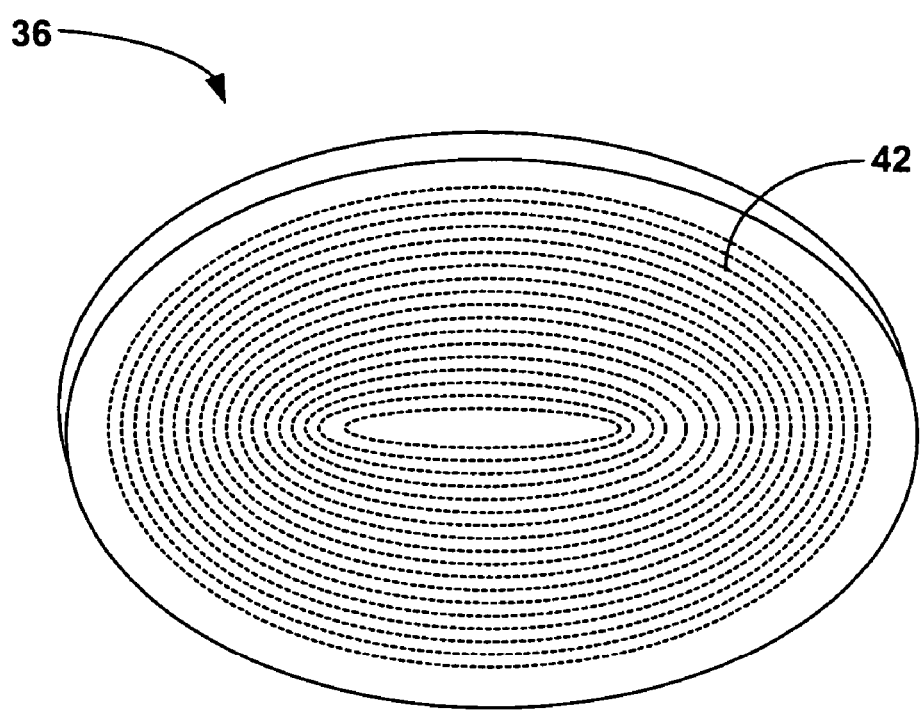
FIG. 4 is top-view diagram illustrating a recharge module of the modular implantable medical device of FIG. 1.

Power source module 32 includes a power source within housing 38. The power source provides power for components of other modules, such as the control electronics within control module 30. The power source may be any power source suitable for use within an IMD, such as one or more batteries, capacitors, solar cells, fuel cells, nuclear cells, or any combination thereof. In an exemplary embodiment, the power source comprises a rechargeable Lithium Ion battery, which may have a thin wound coil construction, or a foil pack or other non-coiled construction to more easily fit within housing 38 which may be less than 5 millimeters thick with an approximately one square inch surface area. Housing 38 may be hermetic, and may be formed of titanium, stainless steel, or a ceramic. Power source module 32 may include an insulator within housing 38 to isolate housing 38 from the power source.

Where the power source includes a rechargeable power, such as a rechargeable battery and/or a capacitor, modular IMD 10 may include recharge module 34. As shown in FIG. 4, recharge module 34 includes a recharge coil 42 within housing 40. Recharge coil 42 inductively receives energy from an external recharging unit (not illustrated) through the skin of patient 14 to recharge the power source. Recharge coil 42 may be formed of windings of copper or another highly conductive material. Housing 40 need not be hermetic, and may be formed of materials such as silicone, polymers and ceramics.

Housings 36, 38 and 40 may have any shape, including the round, coin shape and rectangular shapes with rounded edges illustrated in FIG. 3. Further, one or more surfaces of one or more of housings 36, 38 and 40 may be concave along at least one axis, and preferably two axes. Further details regarding the concavity of housings 36, 38 and 40 may be found in a commonly-assigned U.S. patent application entitled "CONCAVITY OF AN IMPLANTABLE MEDICAL DEVICE," assigned U.S. Ser. No. 10/731,867.

Modules 30, 32 and 34 can be configured in a variety of ways, and the configuration illustrated in FIG. 3 is merely exemplary. Additional exemplary configurations are illustrated in FIGS. 6A, 6B, 9A, 9B, 10, 11A, 11B, 12, 14A and 14B, which are discussed below. Further, modular IMD 10 can include any number of modules, and may include other types of modules instead of or in addition to a power source module 32 and a recharge module 34. For example, modular IMD 10 can include additional power source modules, modules that include additional memory that is accessible by the control electronics within control module 30, modules that include reservoirs for storing therapeutic agents and pumps for delivering therapeutic agents to patient 14, and modules that include sensors sensing physiological parameters, such as pressures or blood flows, or the activity level of patient 12.

Power source module 32 is coupled to control module 30 by a flexible interconnect member 44, which encloses a conductor that allows transmission of energy from the power source of power source module 32 to components such as the control electronics within control module 30. In embodiments where energy is transferred via a DC voltage on the conductor, it may be necessary to make flexible interconnect member 44 hermetic. In embodiments in which flexible interconnect member 44 is hermetic, flexible interconnect member 44 may be made of titanium or stainless steel. In embodiments where energy is transferred via a charge-balance voltage on the conductor, such as an AC voltage, flexible interconnect member 44 need not be hermetic, and may be made of any material including silicone or various polymers.

In the illustrated embodiment, the control electronics of control module 30 regulates the recharging and discharging of the power source within power source module 32. Consequently, as shown in FIG. 3, recharge module 34 is coupled to control module 30 by a flexible interconnect member 46 that encloses a conductor that allows transmission of energy inductively received by coil 42 to control module 30. Because the energy is transferred on the conductor via a charge-balanced voltage, flexible interconnect member 46 need not be hermetic, and may be made of any material including titanium, stainless steel, ceramics, silicone or various polymers.

Interconnect members 44 and 46 are flexible. In some embodiments, as indicated above, interconnect members 44 and 46 are made of a flexible material such as silicone or a flexible polymer. In embodiments where flexible member 44 is hermetic and made of substantially less flexible material, such as titanium or stainless steel, the flexibility of interconnect member 44 is provided by the configuration and/or construction of flexible interconnect member 44.

Interconnect member 44 is flexible in a plurality of directions to provide modules 30 and 32 with multiple degrees of freedom of motion with respect to each other. In exemplary embodiments, interconnect member 44 provides at least three degrees of motion, and the degrees of motion provided include rotational motion. Further details regarding the configuration and/or construction of interconnect member 44 to provide such flexibility may be found in a commonly-assigned U.S. patent application entitled "COUPLING MODULE OF A DISTRIBUTED MODULAR IMPLANTABLE MEDICAL DEVICE," assigned U.S. Ser. No. 10/731,699.

As shown in FIG. 3, modular IMD 10 includes an overmold 48, which may be flexible. In the illustrated embodiment, overmold 48 at least partially encapsulates each of housings 36, 38 and 40. Overmold 48 integrates modules 30, 32 and 34 into a desired form factor, but, where flexible, allows relative intermodule motion. In some embodiments, overmold 48 incorporates mechanical features to restrict intermodule motion to certain directions or within certain ranges. Overmold 48 may be made from silicone, and is some embodiments may be made from two or more materials of differing flexibility, such as silicone and a polyurethane. An exemplary polyurethane for this purpose is Tecothane®, which is commercially available from Hermedics Polymer Products, Wilmington, Mass.

Overmold 48 can be shaped to contour to cranium 12, e.g., may be concave along at least one axis, and may be contoured at its edges to prevent skin erosion on the scalp of patient 14. The flexibility and shape of overmold 48 may improve the comfort and cosmetic appearance of modular IMD 10 under the scalp. Further details regarding the overmold, the concavity of the flexible overmold, and techniques for restricting intermodular motion in a modular IMD 10 may be found in a commonly-assigned U.S. patent application entitled "OVERMOLD FOR A MODULAR IMPLANTABLE MEDICAL DEVICE," assigned U.S. Ser. No. 10,730,873, and a commonly-assigned U.S. patent application entitled "REDUCING RELATIVE INTERMODULE MOTION IN A MODULAR IMPLANTABLE MEDICAL DEVICE," assigned U.S. Ser. No. 10/731,881.

In the illustrated embodiment, modular IMD 10 also includes lead connector modules 50A and 50B (collectively "lead connector modules 50") formed within overmold 48 to receive leads 16 or lead extensions coupled to leads 16. Conductors 52 extend from lead connector modules 50 to hermetic feedthroughs (not illustrated) within housing 36 of control module 30. Lead connector modules 50 may be formed anywhere within overmold 48. In embodiments where overmold 48 includes a rigid material in addition to a flexible material, the rigid material may form at least part of lead connector modules 50 to secure leads 16 or lead extensions, and to protect conductors 52 from damage that may result from flexing within overmold 48.

Figure 5:
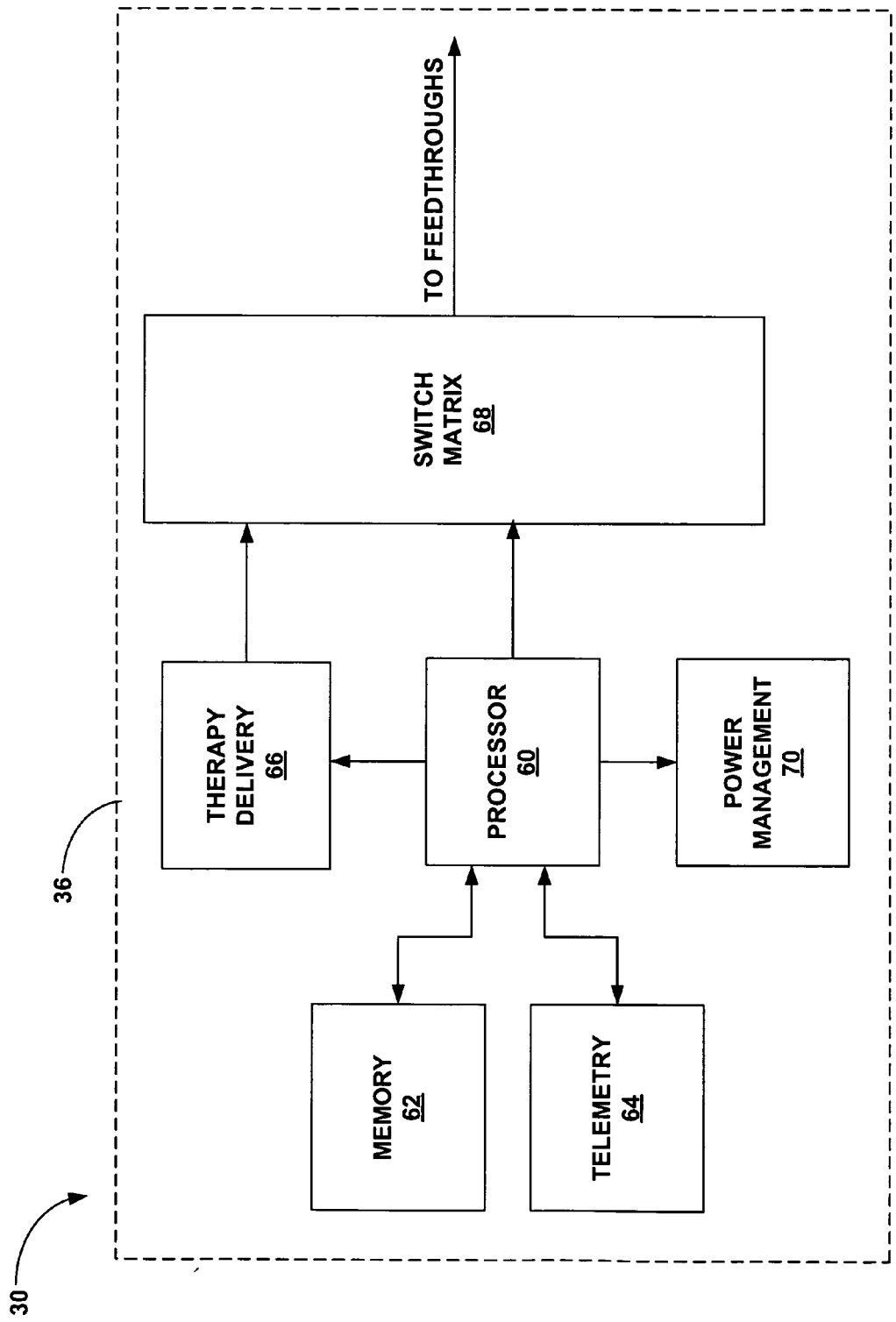
FIG. 5 is a block diagram illustrating a control module of the modular implantable medical device of FIG. 1.

FIG. 5 is a block diagram illustrating control module 30 of modular IMD 10. As described above, control module 30 includes control electronics that control the functioning of modular IMD 10 within housing 36. The control electronics include a processor 60, which may take the form of a microprocessor, digital signal processor (DSP), application specific integrated circuit (ASIC), field-programmable gate array (FPGA), or other logic circuitry.

Control module 30 also includes a memory 62, such as a read-only memory (ROM), random access memory (RAM), electronically-erasable programmable ROM (EEPROM), flash memory, or the like. Memory 62 may store program instructions that may be executed by processor 60 and thereby control the functioning of modular IMD 10. Processor 60 may also store data collected during treatment and/or monitoring of patient 14 within memory 62.

In some embodiments, control module 30 includes telemetry circuitry 64, which enables processor 60 to communicate with other devices such as an external programming device via radio-frequency communication. Telemetry circuitry 64 may include a telemetry coil (not illustrated), which may be fabricated of windings of copper or another highly conductive material. The configuration and location of telemetry coil within housing 36 may be dictated by the available space within housing 36 and the communication requirements of telemetry circuitry 64. Further detail regarding the configuration and location of the telemetry coil may be found in a commonly-assigned U.S. patent application entitled "LOW-PROFILE IMPLANTABLE MEDICAL DEVICE," assigned U.S. Ser. No. 10/730,877.

In some embodiments modular IMD 10 delivers electrical stimulation, and more particularly, control module 30 includes therapy delivery circuitry 66 within housing 36 that generates electrical stimulation. In exemplary embodiments, therapy delivery circuitry 66 comprises circuits for the generation of electrical stimulation in the form of pulses, such as capacitors and switches. In embodiments in which modular IMD 10 is a neurostimulator coupled to leads 16 that include a plurality of electrodes, therapy delivery circuitry 66 may deliver the pulses to a switch matrix 68, which comprises an array of switches. In such embodiments, processor 60 interacts with switch matrix 68 to select electrodes for delivery of generated stimulation pulses. Based on the selections made by processor 60, switch matrix 68 delivers the pulses to conductors that pass through feedthroughs in housing 36 and to electrical contacts on leads 16 that are electrically coupled to the desired electrodes carried by leads 16.

The illustrated components of control module 30 receive energy from the power source within power source module 32 via interconnect member 44 (FIG. 3). In some embodiments in which the power source is rechargeable, control module 30 receives energy inductively captured by recharge module 34 via interconnect member 46, and includes power management circuitry 70 that controls the recharging and discharging of the power source. Power management circuitry 70 may ensure that the power source is not overcharged, over-discharged, or harmed. In some embodiments, power management circuitry 70 includes circuits to measure voltages, currents or temperatures associated with the power source, or rates of change of these parameters, and controls recharging and discharging according to the measured values. Power management circuitry 70 may also include circuits, such as rectifier circuits, for converting charge-balanced voltages, e.g., AC voltages, provided by recharge coil 42 (FIG. 4) into DC voltages for recharging the power source.

Figure 6:
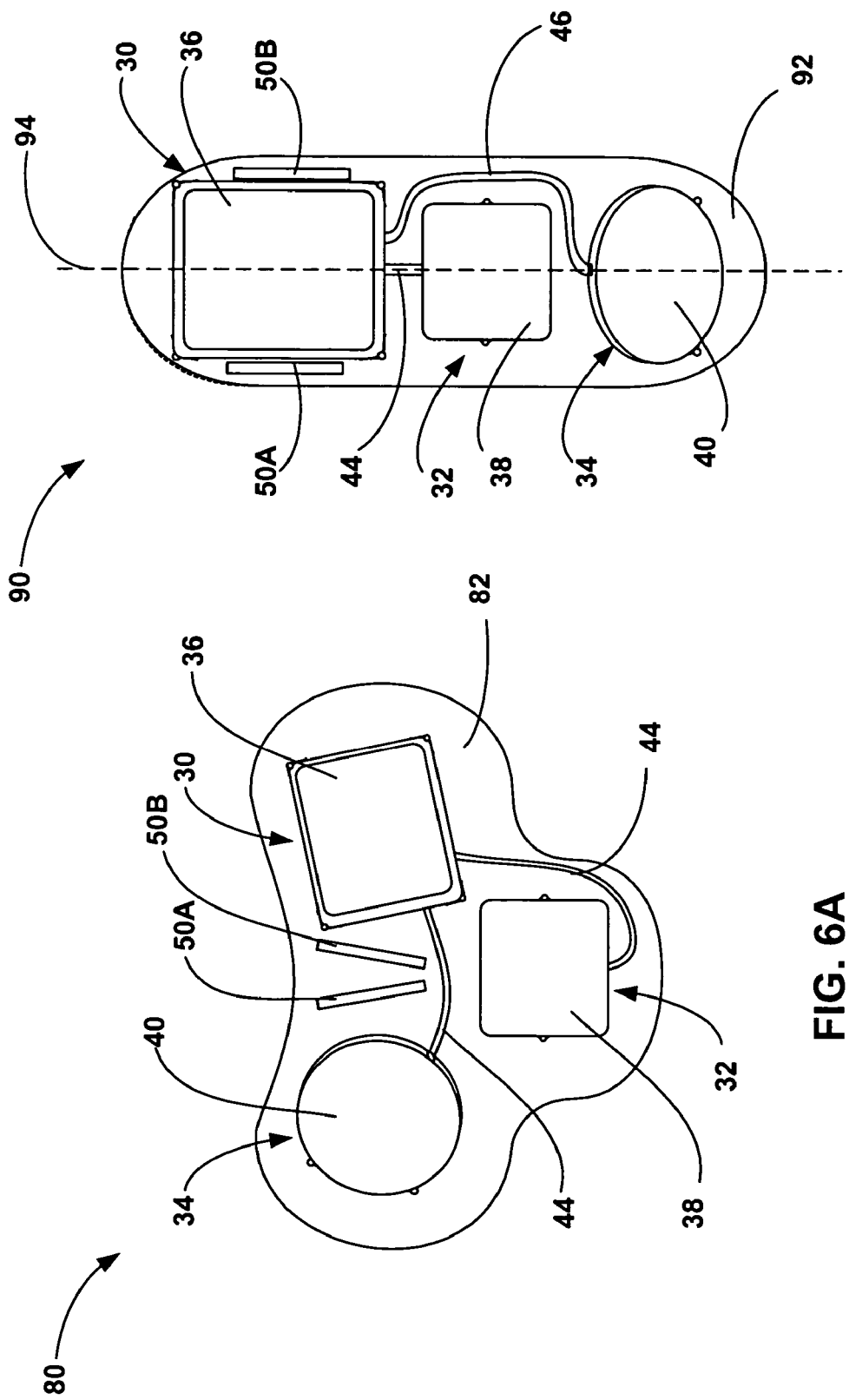
FIGS. 6A and 6B are top-view diagrams illustrating other example modular implantable medical devices.

FIGS. 6A and 6B are top-view diagrams illustrating other example modular IMDs 80 and 90, respectively. More particularly, FIGS. 6A and 6B illustrate modular IMDs 80 and 90 that include alternative arrangements of modules 30, 32 and 34, flexible interconnect members 44 and 46, and lead connection modules 50. Further, FIGS. 6A and 6B illustrate alternatively shaped overmolds 82 and 92, respectively, that at least partially encapsulate modules 30, 32 and 34 of IMDs 80 and 90.

FIGS. 3 and 6A illustrate substantially triangular configurations of modules 30, 32 and 34 within modular IMDs 10 and 80, respectively. Further, overmolds 48 and 82 of IMDs 10 and 80 have substantially triangular shapes. Substantially triangular configurations of modules 30, 32 and 34 and substantially triangularly shaped overmolds such as overmolds 48 and 82 may be preferred for some implantations, such as that described with reference to FIG. 2, in order to reduce the depth of the pocket formed under the scalp of patient 14. Reduced pocket depth may allow for easier explant of modular IMDs 10 and 80 in the event explant is required. However, other configurations are possible, such as the substantially linear configuration of modules 30, 32 and 34 within modular IMD 90 illustrated FIG. 6B.

Although illustrated in FIGS. 3, 6A and 6B as connecting recharge module 34 to control module 30, in some embodiments flexible interconnect member 44 directly connects recharge module 34 to power source module 32. Consequently, in such embodiments power source module 32 includes circuitry to control the recharging and discharging of the power source instead of, or in addition to power management circuit 70 within control module 30.

Figure 7:
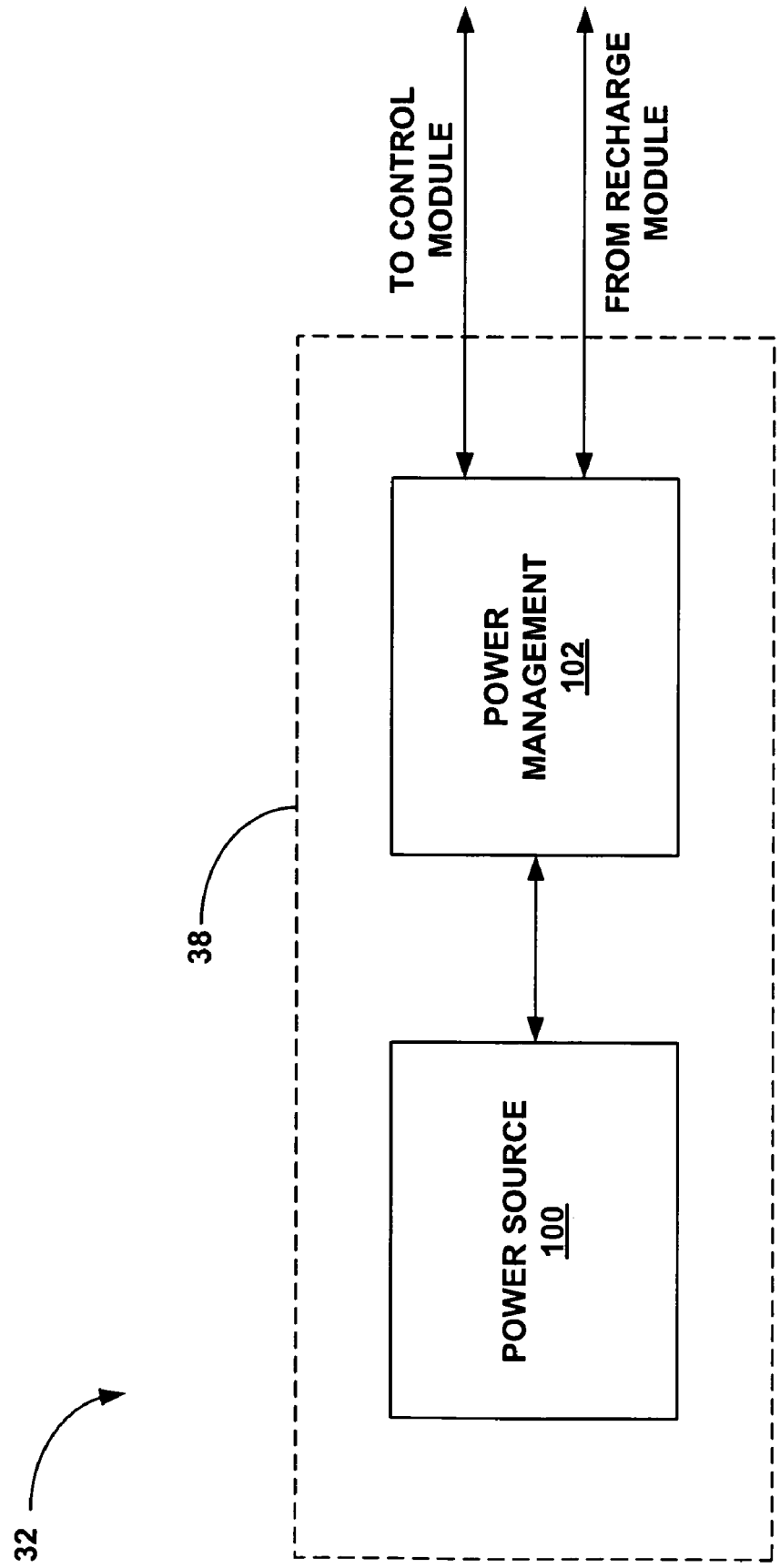
FIG. 7 is a block diagram illustrating a power source module of the modular implantable medical device of FIG. 6B.

FIG. 7 is a block diagram illustrating power source module 32 of modular IMD 90. Power source module 32 includes a rechargeable power source 100 within housing 38, which may include a battery and/or a capacitor. In the illustrated embodiment in which power source module 32 directly receives energy inductively captured by recharge module 34 via flexible interconnect member 44, power source module 32 also include power management circuit 102 that controls the recharging and discharging of power source 100. As described above with reference to power management circuitry 70 illustrated in FIG. 5, power management circuitry 102 may ensure that power source 100 is not overcharged, over-discharged, or harmed. In some embodiments, power management circuitry 102 includes circuits to measure voltages, currents or temperatures associated with power source 100, or rates of change of these parameters, and controls recharging and discharging of power source 100 according to the measured values.

Power management circuitry 102 may also include circuits, such as rectifier circuits, for converting charge-balanced voltages, e.g., AC voltages, provided by recharge coil 42 (FIG. 4) into DC voltages for recharging power source 100. In some embodiments in which interconnect member 44 is non-hermetic, power management circuit 102 includes modulating circuits, i.e., circuits that enable power management circuit 102 to deliver energy to control module 30 in the form of charge-balanced voltages on a conductor. In such embodiments, control module 30 includes circuits, such as rectifier circuits, to convert the charge-balanced voltages to DC voltages for use by components of control module 30.

Figure 8A:
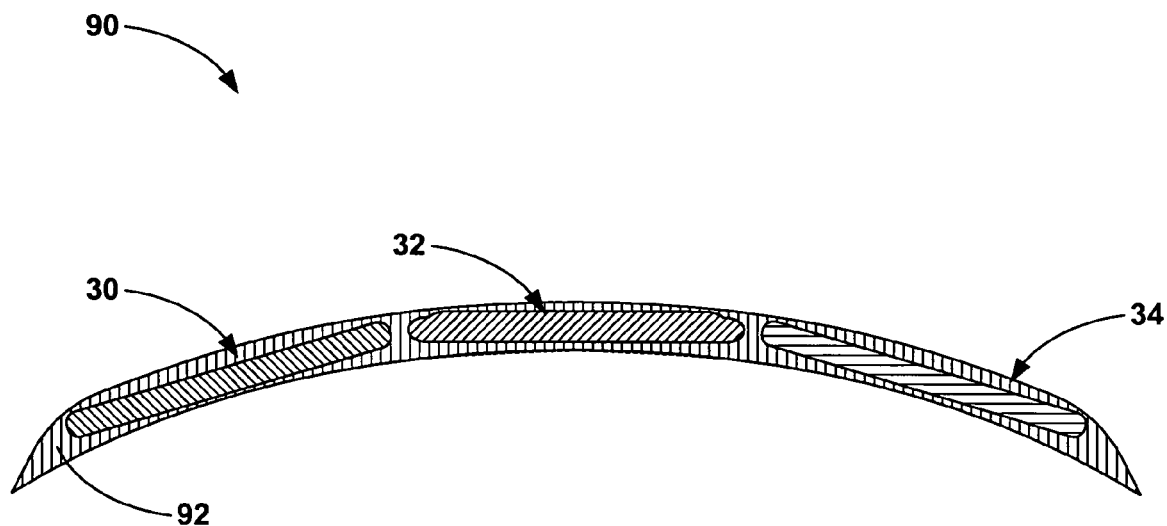
FIGS. 8A and 8B are cross-sectional diagrams illustrating two example configurations of the modular implantable medical device of FIG. 6B.
Figure 8B:
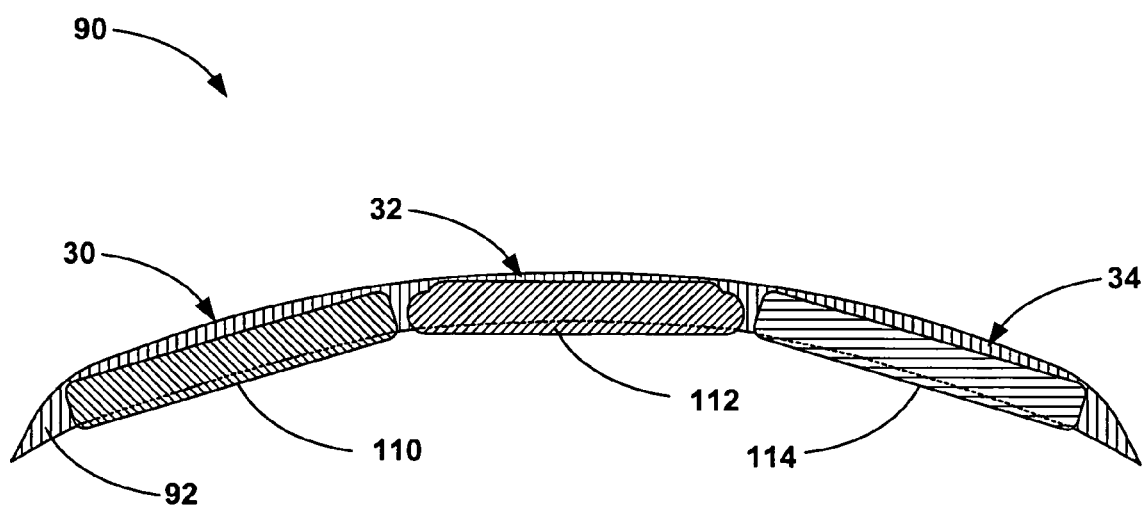

FIGS. 8A and 8B are cross-sectional diagrams illustrating two example configurations of overmold 92 of modular IMD 90, the cross-section taken along axis 94 (FIG. 6B). FIG. 8A illustrates an embodiment of IMD 90 in which overmold 92 fully encapsulates modules 30, 32 and 34, while FIG. 8B illustrates an embodiment of IMD 90 in which overmold 92 partially encapsulates modules 30, 32 and 34. In embodiments where overmold 92 partially encapsulates modules 30, 32 and 34, overmold 92 leaves portions 110, 112 and 114 of modules 30, 32 and 34 exposed, respectively. Portions 110, 112 and 114 may, as illustrated in FIG. 8B, be lower portions of modules 30, 32 and 34, e.g., portions of the modules that are proximate to cranium 12 when modular IMD 90 is implanted thereon.

Embodiments in which overmold 92 fully encapsulates modules 30, 32 and 34 may be preferred as providing greater patient comfort and protection of the modules. However, in some embodiments in which portions 110, 112 and 114 are exposed, troughs may be drilled into the surface of cranium 12 that are sized to receive the portions. By recessing portions 110, 112 and 114 into such troughs, the height of modular IMD 90 above cranium 12 may be reduced.

Figure 9A:
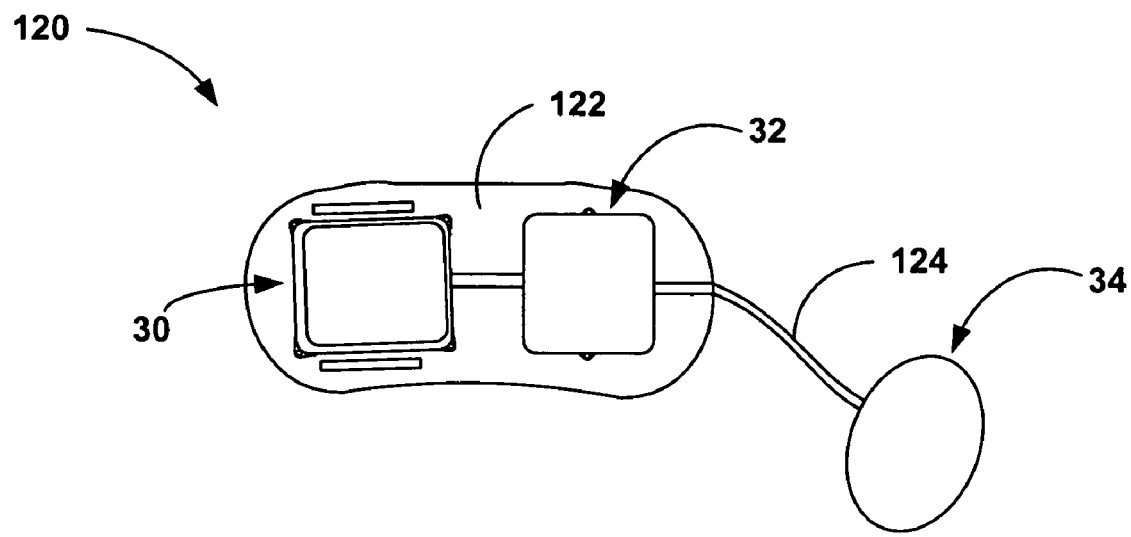
FIGS. 9A and 9B are top-view diagrams illustrating another example modular implantable medical device that include a tethered recharge module.
Figure 9B:
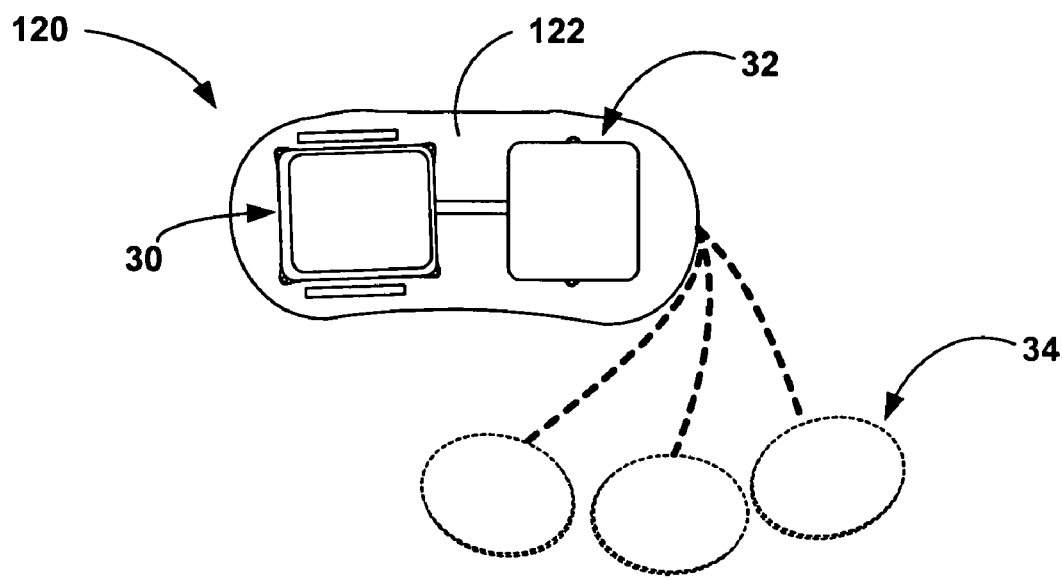
Figure 10:
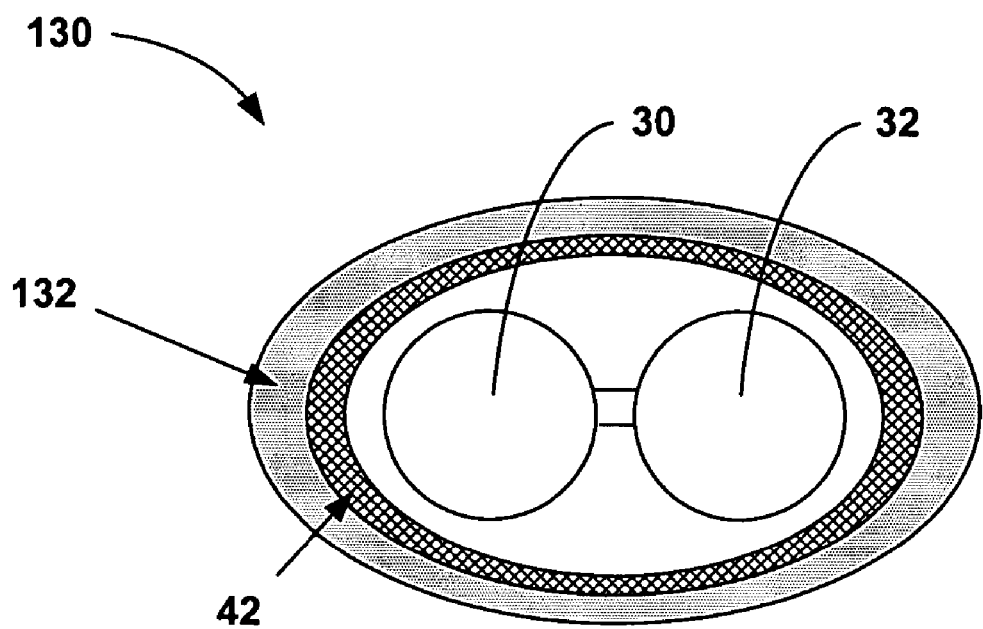
FIGS. 10, 11A, 11B and 12 are conceptual diagrams illustrating other example modular implantable medical devices.

FIGS. 9A and 9B are top-view diagrams illustrating another example modular IMD 120. In the illustrated embodiment, recharge module 34 is not encapsulated by overmold 122, but is instead tethered to overmold 122 by a flexible tether member 124. Flexible tether member 124 is made of a flexible material, such as silicone, to allow substantial movement of recharge module 34 relative to other modules 30 and 32 as illustrated in FIG. 9B. In some embodiments, flexible tether member 124 is shaped as a helix to allow recharge module freedom of movement some significant distance away from other modules 30 and 32. Recharge module 34 can be moved to improve inductive coupling for energy transfer and/or the cosmetics of modular IMD 120 when implanted on cranium 12.

FIGS. 10, 11A, 11B and 12 are conceptual diagrams illustrating other example modular IMDs 130, 140 and 150. Modular IMD 130 of FIG. 10 does not include recharge module 34. Rather, recharge coil 42 is embedded within overmold 132, and surrounds control module 30 and power source module 32.

Figure 11:
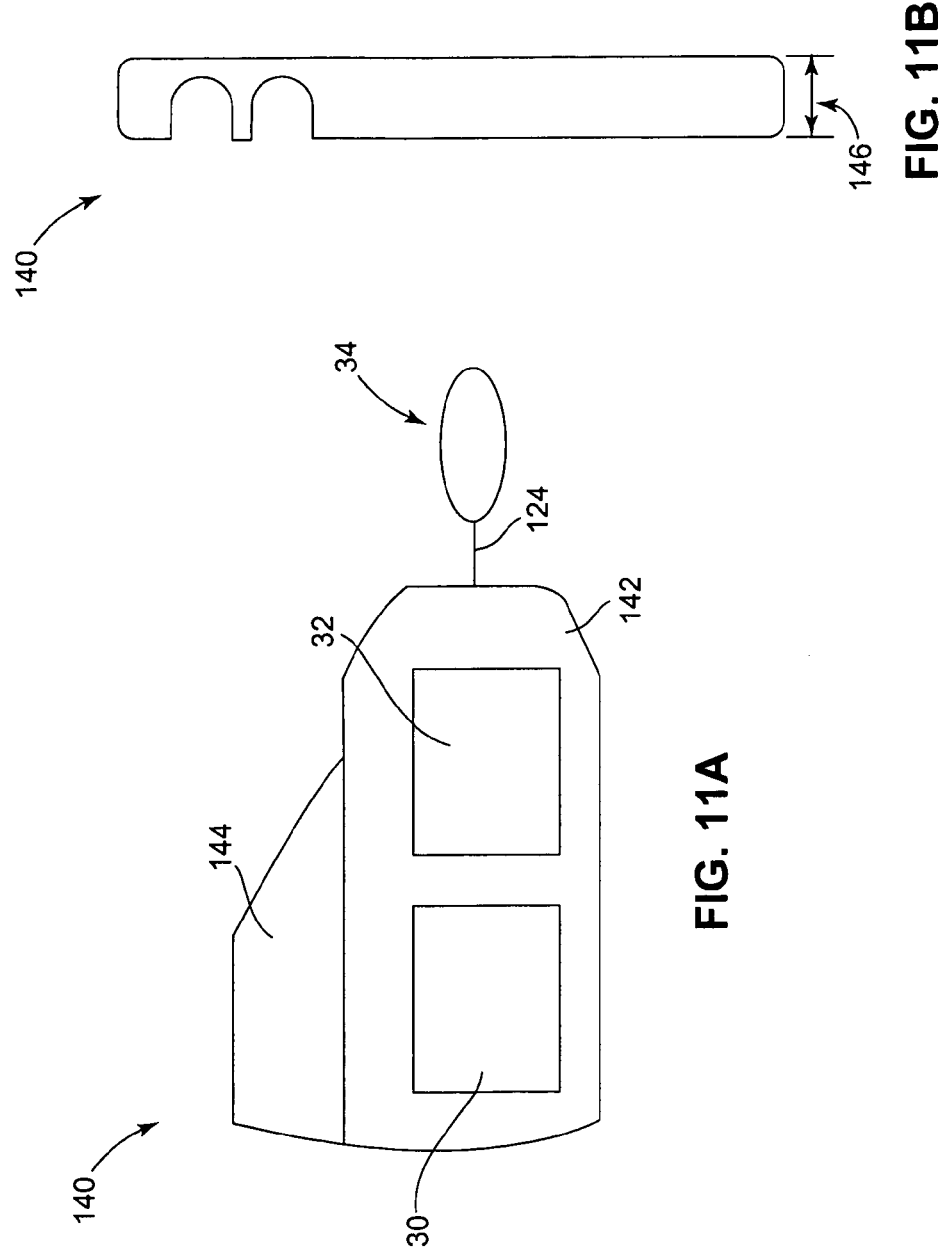

In some embodiments, such as modular IMD 140 illustrated in FIGS. 11A and 11B, control module 30 and power source module 32 are not separately housed. Rather, as illustrated in FIG. 11A, modular IMD 140 includes a single housing 142 to house both control module 30 and power source module 32. Housing 142 may be hermetic and formed of titanium, stainless steel, or a ceramic. Recharge module 34 may, as shown in FIG. 11A, be tethered to housing 142 by flexible tether member 124 so that recharge module 34 can be moved freely relative to housing 142. Further, modular IMD 140 may, as shown in FIG. 11A, include a ceramic connector block 144 to receive leads 16.

FIG. 11B illustrates a side-profile of modular IMD 140. Housing 142 may be a low-profile housing with a thickness 146 that is approximately less than or equal to 6 millimeters. Techniques for arranging components of an IMD to enable a low-profile housing may be found in the commonly-assigned U.S. patent application entitled "LOW-PROFILE IMPLANTABLE MEDICAL DEVICE," assigned U.S. Ser. No. 10/730,877. A low-profile housing 142 may allow modular IMD 140 to be implanted, for example, within an upper buttocks region of patient 14.

Figure 12:
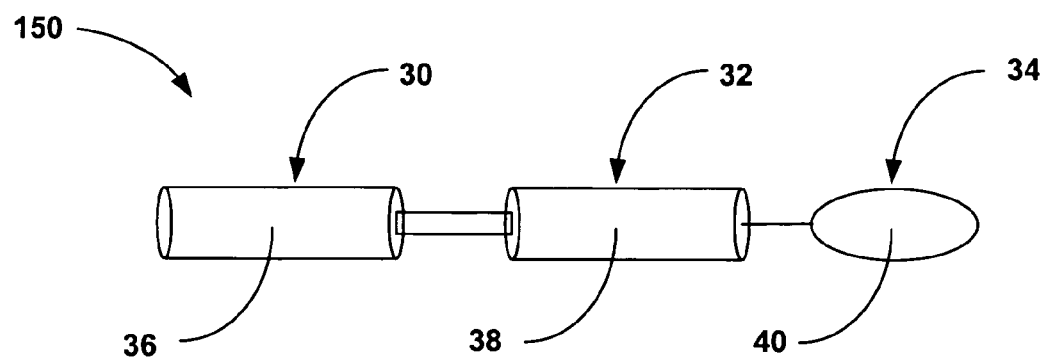

FIG. 12 is a conceptual diagram illustrating a modular IMD 150 in which housing 36 of control module 30 and housing 38 of power source module 32 have substantially cylindrical shapes. The substantially cylindrical shapes of control module 30 and power source module 32 may enable IMD 150 to be implanted within the periphery, e.g., the limbs, of patient 14.

Figure 13:
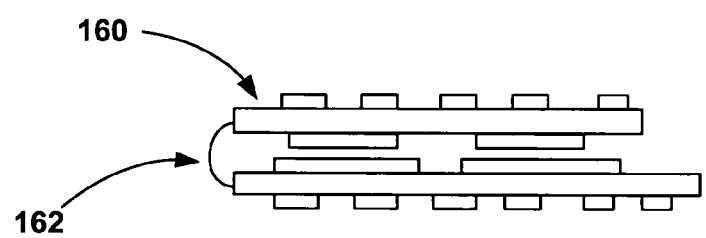
FIG. 13 is a conceptual diagram illustrating a stacked circuit board.

As illustrated in FIG. 13, a circuit board 160 within control module 30 may include flex tape regions 162 that enable the circuit board 160 to have a "stacked" configuration. The stacked configuration of circuit board 160 can enable circuit board 160 to fit within cylindrical housing 36 illustrated in FIG. 12. In some embodiments, circuit board 160 may be constructed entirely of flex tape, and may be have a "rolled" configuration that can enable circuit board 160 to fit within cylindrical housing 36 illustrated in FIG. 12. A variety of primary and rechargeable batteries that have substantially cylindrical shapes are commercially available, and can be used as a cylindrically-shaped power source module 32.

Figure 14A:
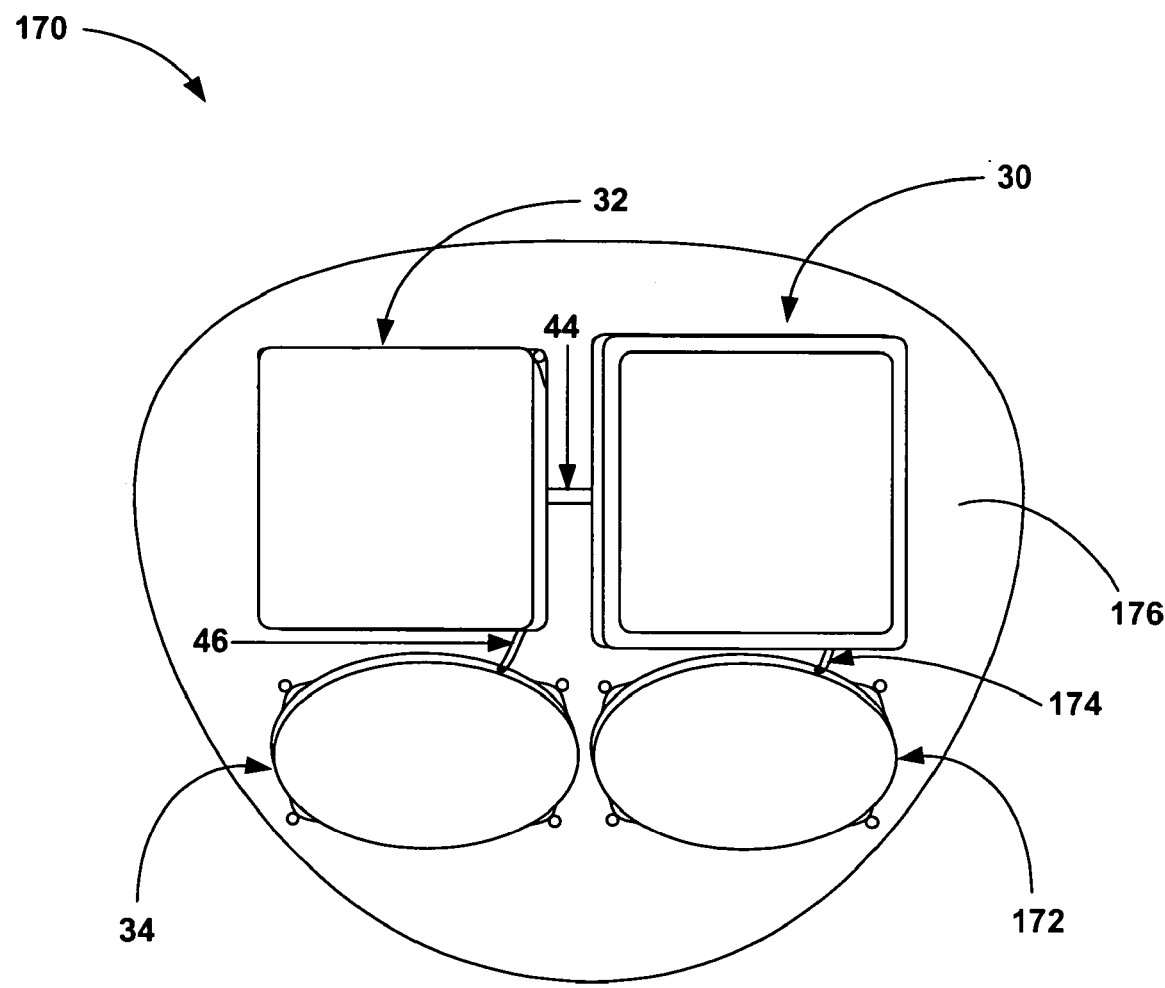
FIGS. 14A and 14B are top-view diagrams illustrating other modular implantable medical devices.
Figure 14B:
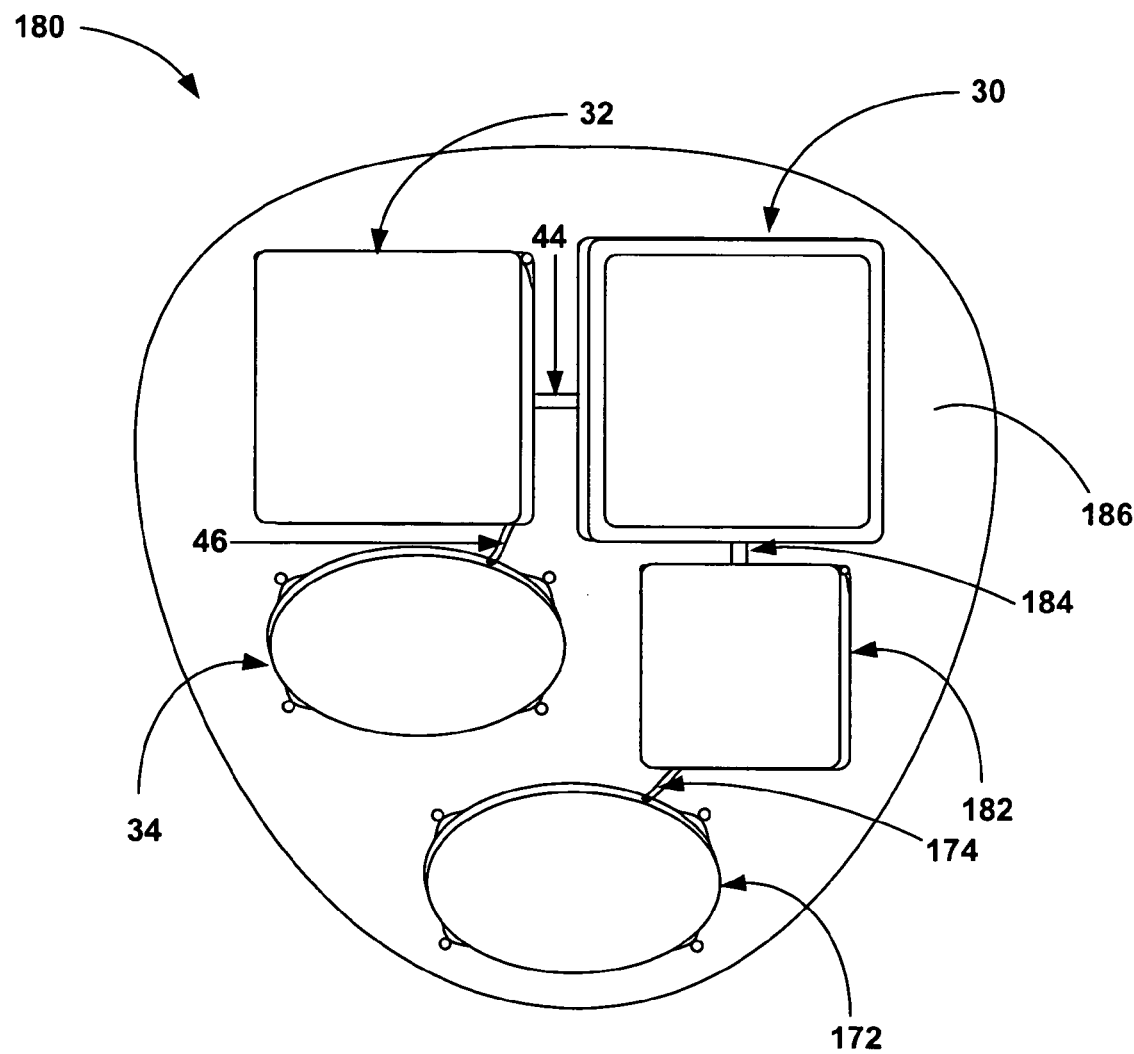

FIGS. 14A and 14B are top-view diagrams illustrating other example modular IMDs 170 and 180. Modular IMDs 170 and 180 include at least one module in addition to control module 30, power source module 32, and recharge module 34. In particular, instead of or in addition to delivering electrical stimulation, modular IMDs 170 and 180 deliver one or more therapeutic agents to patient 14.

Modular IMDs 170 and 180 may be coupled to one or more catheters for delivery of the therapeutic agent to patient 14. Modular IMD 170 includes a reservoir module 172 that contains the therapeutic agent within a housing. The housing may contain a bladder that holds the therapeutic agent, and may provide access to the bladder for refilling. The housing may be formed of, for example, titanium, stainless steel,. a ceramic, a polymer, or silicone.

In such embodiments, control module 30 includes a pump (not shown), and processor 60 (FIG. 5) controls delivery of the therapeutic agent by the pump. The pump within control module 30 receives the therapeutic agent from reservoir module 172 via a flexible interconnect member 174 that includes to enable transfer of the therapeutic agent. Flexible interconnect member 174 need not be hermetic, and may be made from, for example, titanium, stainless steel, a ceramic, a polymer, or silicone. An overmold 176 may at least partially encapsulate the housing of reservoir module 172 in addition to the housings of control module 30, power source module 32, and recharge module 34.

Modular IMD 180 illustrated in FIG. 14B includes a separately housed pump module 182 that includes a pump. The pump within pump module 182 may be used to deliver the therapeutic agent within reservoir module 172 instead of or in addition to a pump within control module 30. In the illustrated embodiment, pump module 182 rather than control module 30 is coupled to reservoir module 172 by flexible interconnect member 174, and the pump within pump module 182 receives the therapeutic agent within reservoir module 172 via a lumen within flexible interconnect member 174.

The housing of pump module 182 may be made from, for example, titanium, stainless steel, or a ceramic. A flexible interconnect member 184 carries one or more conductors used by processor 60 (FIG. 5) to control the delivery of the therapeutic agent to patient 14 by the pump within pump module 182. The flexible interconnect member 184 may need to be hermetic, and may be made from, for example, titanium, stainless steel, or a ceramic. A flexible overmold 186 may at least partially encapsulate the housings of reservoir module 172 and pump module 182, in addition to the housings of control module 30, power source module 32, and recharge module 34.

FIGS. 15–21 show various exemplary embodiments of modules and the overmold wherein at least one of the modules is partially covered by the overmold with a portion of the module extending out of the overmold for receipt into a recess formed in the cranium of the patient. In a preferred embodiment, the recess in the cranium is the shape of a cylinder. Therefore, in a preferred embodiment the module intended for receipt in the recess is also cylindrical. These embodiments may be implemented in many different configurations of the modules including, but not limited to, linear, triangular, square, rectangular, or other shapes. It should also be noted that the recess in the cranium for receipt of one or more modules may extend all the way through the cranium or it may extend only partially through the cranium. For example, the recess may only extend through the outer table of the cranium to preserve structural integrity of the cranium.

The embodiments of FIGS. 15–21 may be utilized in conjunction with the other features and components described above with respect to the other embodiments and figures.

Figure 15:
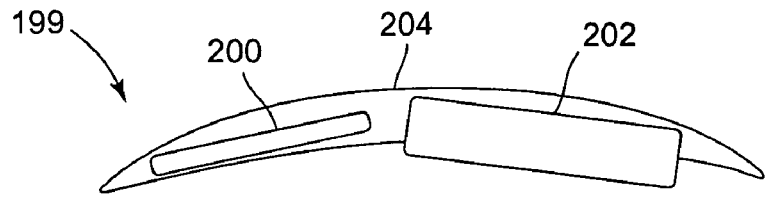
FIG. 15 is a cross-sectional diagram illustrating an exemplary embodiment of a modular implantable medical device.

FIG. 15 shows an implantable medical device 198, including module 200 that is covered by the overmold 204 and module 202 that is partially covered by overmold 204. With this embodiment implantable medical device, the module 202 may be received into a recess in the cranium while the module 200 is placed between the cranium and the scalp.

Figure 16:
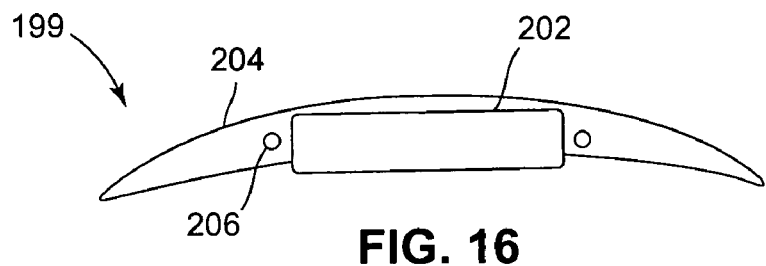
FIG. 16 is a cross-sectional diagram illustrating another exemplary embodiment of a modular implantable medical device.
Figure 17:
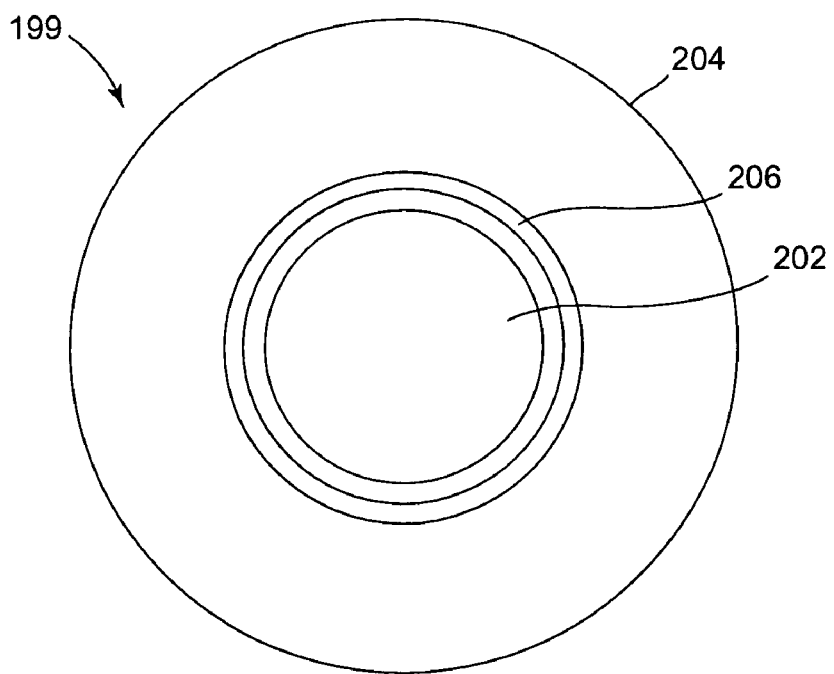
FIG. 17 is a top-view diagram of the embodiment of FIG. 16.

FIGS. 16–17 show an implantable medical device 199, including module 202 that is partially covered by overmold 204 and module 206 that is covered by overmold 204. In this embodiment, module 206 is a recharge coil or telemetry coil or both.

Figure 18:
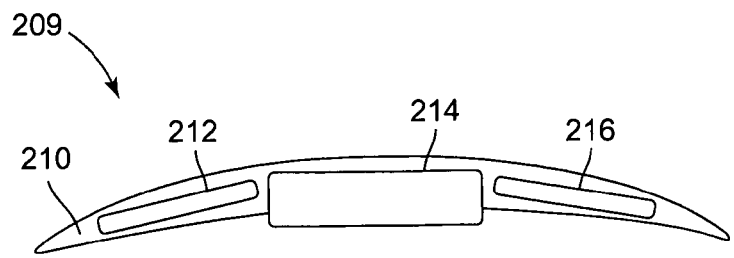
FIG. 18 is a cross-sectional diagram illustrating another exemplary embodiment of a modular implantable medical device.

FIG. 18 shows an implantable medical device 209. Device 209 includes modules 212, 214 and 216. Modules 212 and 216 are covered by the overmold 210. Module 214 is partially covered by overmold 210 so that it can be partially recessed into a recess in the cranium.

Figure 19:
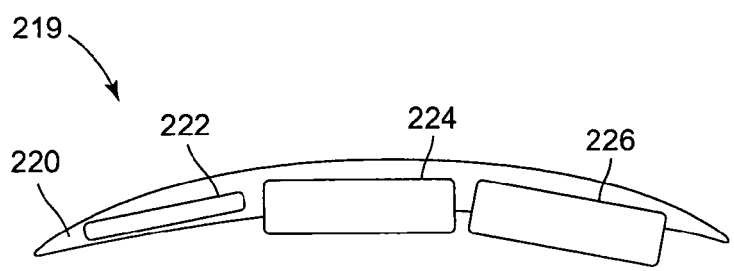
FIG. 19 is a cross-sectional diagram illustrating another exemplary embodiment of a modular implantable medical device.

FIG. 19 shows an implantable medical device 219. Device 219 includes modules 222, 224 and 226. Module 222 is covered by the overmold 220. Modules 224 and 226 are partially covered by overmold 220 for receipt in one or more recesses in a cranium.

Figure 20:
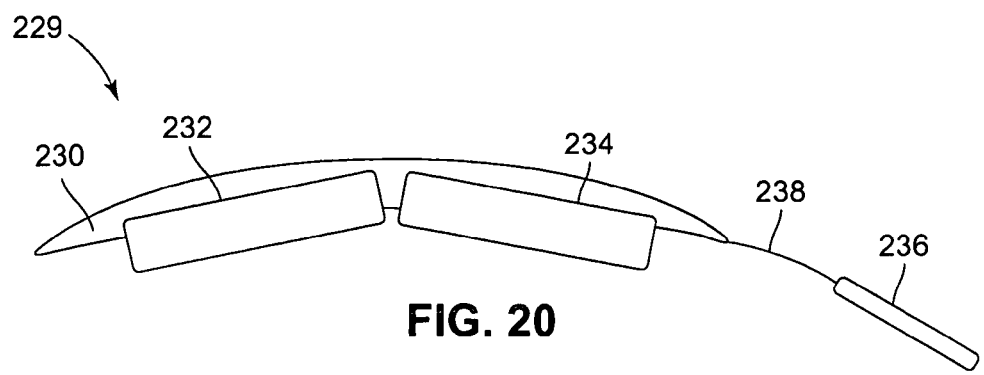
FIG. 20 is a cross-sectional diagram illustrating another exemplary embodiment of a modular implantable medical device.

FIG. 20 shows an implantable medical device 229. Device 229 includes modules 232 and 234 partially covered by overmold 230. A third module 236 is connected to the overmold 230 by tether 238. In a preferred embodiment module 236 is a recharge coil in a housing.

Figure 21:
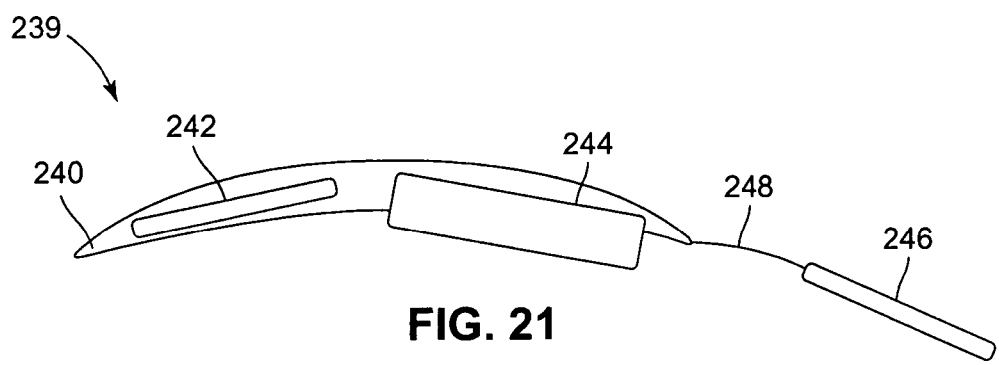
FIG. 21 is a cross-sectional diagram illustrating another exemplary embodiment of a modular implantable medical device.

FIG. 21 shows an implantable medical device 239. Device 239 includes modules 242, 244 and 246. Module 242 is covered by overmold 240. Module 244 is partially covered by overmold 240. Module 246 is connected to the overmold 240 by tether 248. In a preferred embodiment module 246 is a recharge coil in a housing.

Various embodiments of the invention have been described. These and other embodiments are within the scope of the following claims.

The invention claimed is:

1. An implantable medical device for implantation in the head of a patient comprising:
   a first module including a first module housing and first operative component within the first module housing;
   a second module including a second operative component; and
   a flexible overmold that covers the second module and partially covers the first module wherein the first module housing extends out of the overmold for receipt in a first recess in a cranium of a patient.

2. The implantable medical device of claim 1, wherein the first module housing is substantially cylindrical.

3. The implantable medical device of claim 1, wherein the second operative component includes a recharge coil.

4. The implantable medical device of claim 3, wherein the second module includes a second module housing containing the recharge coil.

5. The implantable medical device of claim 1 further comprising a third module that includes a third operative component.

6. The implantable medical device of claim 5, wherein the third module includes a third module housing, and wherein the flexible overmold partially covers the third module wherein the third module housing extends out of the overmold for receipt in a second recess in the cranium of the patient.

7. The implantable medical device of claim 6, wherein the first module housing and the third module housing are each substantially cylindrical.

8. The implantable medical device of claim 5 wherein the overmold covers the third module.

9. The implantable medical device of claim 5, wherein the third module is located outside of the overmold, and wherein the implantable medical device further comprises a flexible tether member that connects the third module to the overmold.

10. The implantable medical device of claim 9, wherein the flexible tether member comprises a helix.

11. The implantable medical device of claim 1, wherein the first operative component comprises control electronics and a therapy delivery circuit within the first module housing.

12. The implantable medical device of claim 11, wherein the therapy delivery circuit comprises a pulse generator.

13. The implantable medical device of claim 12, wherein the first operative component further comprises a power source within the first module housing, wherein the power source provides power to the control electronics and therapy delivery circuit.

14. The implantable medical device of claim 13, wherein the power source is rechargeable.

15. The implantable medical device of claim 14, wherein the second operative component includes a recharge coil coupled to the power source for recharging the power source.

16. The implantable medical device of claim 15 wherein the recharge coil substantially encircles the first module.

17. The implantable medical device of claim 1, wherein the flexible overmold comprises silicone.

18. The implantable medical device of claim 1, wherein the flexible overmold comprises at least two materials.

19. The implantable medical device of claim 1, further comprising a flexible interconnect member to couple the first and second modules.

20. The implantable medical device of claim 19, wherein the interconnect member is flexible in a plurality of directions and allows the first and second modules to have a plurality of degrees of freedom of movement relative to each other.

21. The implantable medical device of claim 1, wherein the overmold is shaped for implantation on a cranium of a patient.

22. The implantable medical device of claim 1, in which the second module includes a second module housing containing the second operative component, the first module housing has a height $H_1$, the second module housing has a height $H_2$, the height $H_1$ is greater than the height $H_2$ and the first module housing extends out of the overmold for receipt in the first recess in the cranium of the patient.

23. An implantable medical device for implantation in the head of a patient comprising:
   a first module including a first module housing and first operative component within the first module housing, the first module housing having a height $H_1$;
   a second module including a second module housing and second operative component within the second module housing, the second module housing having a height $H_2$; and
   a flexible overmold that covers at least part of at least one of the first module or the second module;
   wherein the height $H_1$ is greater than the height $H_2$ and the first module housing extends out of the overmold for receipt in a first recess in a cranium of a patient.

* * * * *